United States Patent [19]  [11]  4,216,209
Bellini et al.  [45]  Aug. 5, 1980

[54] TRIPEPTIDE ANGIOTENSIN CONVERTING ENZYME INHIBITORS

[75] Inventors: Francesco Bellini, St. Laurent; Hans U. Immer, Mount Royal, both of Canada

[73] Assignee: American Home Products Corporation, New York, N.Y.

[21] Appl. No.: 21,737

[22] Filed: Mar. 19, 1979

[51] Int. Cl.$^2$ ..................... A61K 37/00; C07C 103/52
[52] U.S. Cl. ............................... 424/177; 260/112.5 R
[58] Field of Search .................. 424/177; 260/112.5 R

[56] References Cited
U.S. PATENT DOCUMENTS 4,105,776  8/1978  Ondetti et al. ...................... 424/177

OTHER PUBLICATIONS

Erdös, Federation Proceedings 36, No. 5 (1977) 1760–1765.
Cushman, et al., Biochemistry 16, No. 25 (1977) 5484–5891.
Biological Abstract 65, p. 60613.
Biological Abstract 66, p. 4592.
Biological Abstract 65, p. 66598.
Biological Abstract 65, p. 28660.
Biological Abstract 63, p. 25801.

Primary Examiner—Delbert R. Phillips
Attorney, Agent, or Firm—Arthur E. Wilfond

[57] ABSTRACT

Compounds of the formula $HSCH_2CHR^1CO$—Pro—$R^2$—$R^3$—OH in which $R^1$ is hydrogen or lower alkyl, $R^2$ is an amino acid residue exclusive of prolyl and $R^3$ is an amino acid residue exclusive of glutamyl are useful for alleviating angiotensin related hypertension.

8 Claims, No Drawings

TRIPEPTIDE ANGIOTENSIN CONVERTING ENZYME INHIBITORS

BACKGROUND OF THE INVENTION (a) Field of the Invention

This invention relates to tripeptide derivatives which are characterized by having a N-(thiopropanoyl)-proline residue. The derivatives are antihypertensive agents. The invention also relates to a process for preparing these derivatives, pharmaceutical compositions thereof and to a method for using these derivatives.

(b) Prior Art

The angiotensin-converting enzyme is part of the renin-angiotensin system; for instance, see E. G. Erdos, Federation Proc., 36, 1760 (1977). The enzyme converts angiotensin I to angiotensin II, the most potent naturally occurring pressor substance known. Recently, a number of inhibitors of this enzyme have been found, e.g. see D. W. Cushman et al., Biochemistry, 16, 5484 (1977). One of the more interesting of these inhibitors, 1-(3-mercapto-2-D-methyl-1-oxopropyl)-L-proline (captopril) has been shown to be a clinically effective antihypertensive agent.

The present invention provides compounds which are extremely effective inhibitors of this enzyme.

SUMMARY OF THE INVENTION

The compounds of this invention are represented by formula I

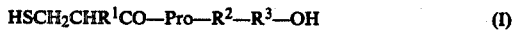

HSCH$_2$CHR$^1$CO—Pro—R$^2$—R$^3$—OH    (I)

in which R$^1$ is hydrogen or lower alkyl; R$^2$ is an amino acid residue exclusive of prolyl and R$^3$ is an amino acid residue exclusive of glutamyl.

A preferred group of compounds is represented by formula I in which R$^1$ is hydrogen or lower alkyl; R$^2$ is an amino acid residue of alanine, arginine, cysteine, glycine, histidine, isoleucine, leucine, lysine, methionine, ornithine, phenylalanine, serine, threonine, tryptophan, tyrosine or valine; and R$^3$ is an amino acid residue of alanine, arginine, cysteine, glycine, histidine, isoleucine, leucine, lysine, methionine, ornithine, phenylalanine, proline, serine, threonine, tryptophan, tyrosine or valine.

Another preferred group of compounds is represented by formula I wherein R$^1$ is hydrogen or methyl. A more preferred group of compounds is represented by formula I in which R$^1$ is hydrogen or methyl and R$^2$ and R$^3$ are selected from the amino acid residues of arginine, histidine, leucine, phenylalanine and serine.

The compounds of formula I are prepared by coupling an acid compound of formula II

R$^4$SCH$_2$CHR$^1$COOH    (II)

in which R$^1$ is as defined hereinbefore and R$^4$ is a sulfhydryl protecting group with a protected tripeptide of formula III

H—Pro—R$^2$—R$^3$—OR$^5$    (III)

in which R$^2$ and R$^3$ are as defined hereinbefore and R$^5$ is a carboxyl protecting group to obtain the corresponding compound of formula IV

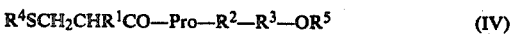

R$^4$SCH$_2$CHR$^1$CO—Pro—R$^2$—R$^3$—OR$^5$    (IV)

in which R$^1$, R$^2$, R$^3$, R$^4$ and R$^5$ are as defined herein, followed by deprotection of the compound of formula IV.

A method also is provided for alleviating angiotension related hypertension in a hypertensive mammal by administering to the mammal an effective dose of the compound of formula I.

The compounds of formula I form a pharmaceutical formulation when admixed with a pharmaceutically acceptable carrier.

DETAILS OF THE INVENTION

In general the abbreviations used herein for designating the amino acids and the protecting groups are based on recommendations of the IUPACIUB Commission on Biochemical Nomenclature, see Biochemistry, 11, 1726–1732 (1972). For instance, Arg, His, Leu, Phe and Ser represents the "residues" of L-arginine, L-histidine, L-leucine, L-phenylalanine and L-serine, respectively. The term "residue" refers to a radical derived from the corresponding L-amino acid by eliminating the hydroxyl of the carboxyl group and one hydrogen of the amino group.

The term "lower alkyl" as used herein means straight chain alkyl radicals containing from one to six carbon atoms, e.g. methyl, ethyl, propyl, butyl, pentyl and hexyl, and branched chain alkyl radicals containing three or four carbon atoms, e.g. isopropyl, isobutyl and tert-butyl.

The compounds of formula I form salts with suitable therapeutically acceptable inorganic and organic bases. These derived salts possess the same activity as the parent acid and are included with the scope of this invention. The acid is transformed in excellent yield into the corresponding therapeutically acceptable salt by neutralization of said acid with the appropriate inorganic or organic base. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxylakyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methyl-pyridinium, N-methyl-N-(2-hydroxyethyl)-morpholinium N,N-dimethylmorpholinium, N-methyl-N-(2-hydroxyethyl)-morpholinium, N,N-dimethyl-piperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of formula I exhibit antihypertensive effects, which are mediated through the properties of the compounds to inhibit angiotensin conversion. In other words, the compounds inhibit the action of the angiotensin converting enzyme (ACE) which transforms angiotensin I to angiotensin II. Hence, the compounds are useful for reducing or relieving angiotensin related hypertension in mammals suffering from such hypertension.

This antihypertensive effect is demonstrated in standard pharmacologic tests, for example, tests conducted in the spontaneously hypertensive rat (SHR).

More specifically exemplified, the antihypertensive effect can be demonstrated in the following test:

Male SHR of the Okamoto-Aoki strain (purchased from Charles River Lakeview, Boston, Mass.) ranging in weight between 280 and 370 g are anesthetized with diethyl ether. Their left femoral arteries and veins are cannulated with polyethylene tubing of the appropriate size. Each animal is then placed in a rubber mesh jacket which is secured with four towel clamps. The animal is suspended via the towel clamps from a bar and allowed to recover from the anesthesia. The arterial cannula is connected to a Statham pressure transducer (Model P23, Gould Statham Instruments, Hato Rey, Porto Rico) which, in turn, is attached to a polygraph for recording arterial blood pressure (BP) and pulse rate.

When the BP has stabilized, the intravenous injection of the agonists, angiotensin I (AI) or bradykinin (B) is initiated. Each of the agonists is prepared daily from refrigerated stock solution (using distilled water as the diluent), and injected in a volume of 1 ml/kg (using physiological saline as the diluent) at the following doses: AI, 0.125 $\mu$g/kg and B, 5 $\mu$g/kg.

Enough time is allowed for the BP to return to preinjection levels before the next agonist is given. A dose of the compound to be tested is given orally seven to ten minutes after the injection of the last agonist. Four rats are used and the test compound is given by gastric gavage in a volume of 5 ml/kg of body weight. Heart rate and BP are measured at 5, 10, 15, 30, 45 and 60 minutes and at hourly intervals thereafter for a period of at least four hours after drug administration. At one and two hours after the test compound has been given, AI and B are injected again at the same concentration and in the same order as during the control period.

When tested according to the preceding method, N-[N-[1-(3-mercapto-1-oxopropyl)prolyl]histidyl]leucine, described in Example 6, caused a 8% decrease in mean arterial BP (measured two hours after its administration), a 564% potentiation of bradykinin response and a 61% reduction in angiotensin I response on BP at a dose of 50 mg/kg of body weight. N-[N-[1-(3-Mercapto-2-D-methyl-1-oxopropyl)prolyl]histidyl]leucine, described in Example 6, caused a 12% decrease in mean arterial BP (measured two hours after its administration), a 689% potentiation of bradykinin response and a 69% reduction in angiotensin I response on BP at a dose of 5 mg/kg of body weight.

When the compounds of formula I of this invention are used as antihypertensive agents in mammals, e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example enough saline or glucose to make the solution isotonic.

The tablet compositions containing the active ingredient in admixture with non-toxic pharmaceutical excipients are, for example, starch, milk, sugar, certain types of clay and so forth. The tablets can be uncoated or they can be coated by known techniques so as to delay disintegration and adsorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacturing of aqueous suspensions. Suitable excipients are, for example, methyl cellulose, sodium alginate, gum acacia, lecithin and so forth. The aqueous suspensions also can contain one or more preservatives, one or more colouring agents, one or more flavouring agents and one or more sweetening agents.

Non-aqueous suspensions can be formulated by suspending the active ingredient in a vegetable oil, for example, arachic oil, olive oil, sesame oil, or coconut oil, or in a mineral oil, for example, liquid paraffin, and the suspension may contain a thickening agent, for example, beeswax, hard paraffin or cetyl alcohol. These compositions also can contain a sweetening agent, flavouring agent or antioxidant.

The dosage of the compounds of formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilogram body weight per day, although as aforementioned variations will occur. However, a dosage level that is in the range from about 0.5 mg to about 100 mg per kilogram body weight per day is employed most desirably in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive theapy. Such antihypertensive therapeutic agents include the thiazide diuretics, e.g., chlorothiazide or hydrochlorothiazide; mineralocorticoid antagonizing diuretic agents, e.g., spironolactone; and other diuretics such as triamterene and furosemide. Examples of still other suitable antihypertensive agents are prazosin, hydralazine and centrally active antihypertensive agents such as methyldopa, clonidine, and reserpine; as well as the $\beta$-adrenergic blocking agents, for instance, propranolol. In this instance, the compound of formula I, or its therapeutically acceptable acid addition salt, can be administered sequentially or simultaneously with the antihypertensive and/or diuretic agent. Preferred antihypertensive therapeutic agents are the antihypertensive agents such as the thiazides, mineralocorticoid antagonizing diuretic agents and the $\beta$-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are described in medical textbooks; for instance, "Physicians' Dest Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt, is administered as described previously.

The compounds of this invention can be prepared by coupling an acid compound of formula II

$$R^4SCH_2CHR^1COOH \qquad (II)$$

or its chemical equivalent, in which $R^1$ is as defined hereinbefore and $R^4$ is a sulfhydryl protective group with a protected tripeptide of formula III

$$H-Pro-R^2-R^3-OR^5 \qquad (III)$$

in which $R^2$ and $R^3$ are as defined hereinbefore and $R^5$ is a carboxylic acid protective group to obtain the corresponding compound of formula IV

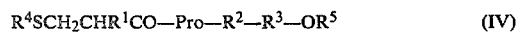

$$R^4SCH_2CHR^1CO-Pro-R^2-R^3-OR^5 \qquad (IV)$$

followed by deprotection of the compound of formula IV to obtain the corresponding compound of formula I.

The acid compound of formula II is prepared by conventional methods, for example, see A. Fredga and O. Martenssen, Ark. Kemi. Mineral. Geol., 16B (No. 8), 1 (1942), see Chem. Abstr., 38, 3616[6] (1944), or can be obtained commercially. The protective group for the sulfhydryl function of this acid can be any of the groups generally used for this purpose in peptide chemistry. Examples of suitable protective groups are acetyl, benzoyl, benzyl, trityl, benzyloxycarbonyl or acetamidomethyl.

The protected tripeptides of formula III are known or are prepared readily from smaller peptides and/or amino acids by a series of condensations involving the reaction of an appropriately protected peptide unit having an activated carboxylic ester with an appropriately protected peptide unit having a free amino group. A number of procedures or techniques suitable for the preparation of the present protected peptide starting materials are described by Immer et al., U.S. Pat. No. 3,917,578, issued Nov. 4, 1975, which is incorporated herein by reference.

Concerning the protecting group ($R^5$) for the carboxylic acid function of the protected tripeptide of formula III, the protecting groups for carboxylic acids usually used in peptide chemistry are suitable. Examples of suitable protecting groups include methyl (represented by OMe), ethyl (represented by OEt), tert-butyl (represented by Bu$^t$) or benzyl (represented by OBzl) esters.

In a preferred method for preparing the compounds of this invention the acid compound of formula II is coupled with the protected tripeptide of formula III by the "activated ester" coupling procedure. Accordingly the acid compound is converted into an activated ester. Descriptions of such carboxyl-activating groups are found in general textbooks of peptide chemistry; for example K. D. Kopple, "Peptides and Amino Acids", W. A. Benjamin, Inc., New York, 1966, pp. 45-51, and E. Schröder and K. Lübke, "The Peptides"; Vol. 1, Academic Press, New York, 1965, pp. 77-128. Examples of the activated form of the terminal carboxyl are acid chloride, anhydride, azide, activated ester, or O-acyl urea of a dialkylcarbodiimide. The following activated esters have proved to be particularly suitable in the process of this invention: 2,4,5-trichlorophenyl (represented by OTcp), pentachlorophenyl (represented by OPcp), p-nitrophenyl (represented by ONp), or 1-benzotriazolyl (represented by OBt); the succinimido group is also useful for such activation.

Thereafter the product of the coupling reaction, the compound of formula IV, is deprotected to afford the corresponding compound of formula I.

The conventional deprotective step or steps are used depending on the particular protective groups $R^4$ and $R^5$. For a review of these methods see Methoden der Organischen Chemie (Houben-Weyl), Vol. XV, part 1, p. 736 (1974). In a preferred process the deprotection is effected by subjecting the compound of formula IV wherein $R^4$ is an "acyl type" protecting group, e.g. acetyl or benzoyl, and $R^5$ is tert-butyl to trifluoroacetic acid in anisole. Hence, the ester group is removed to give the intermediate compound of formula $R^4S-CH_2CHR^1CO-Pro-R^2-R^3-OH$. Thereafter, the alkaline hydrolysis or ammonolysis of the latter compound affords the desired compound of formula I.

The following examples illustrate further this invention.

EXAMPLE 1

Benzyloxycarbonyl-prolyl-histidine, Methyl Ester (Z-Pro-His-OMe)

A solution of N,N¹-dicyclohexylcarbodiimide (DCC, 13.6 g, 66 mmol) in distilled dimethylformamide (DMF, 15 ml) is added dropwise to a cold solution (0° to 5° C.) of Z-Pro-OH (15 g, 60 mmol) and 1-hydroxybenzotriazole (HOBt, 12.16 g, 120 mmol) in distilled DMF (40 ml). The mixture is stirred at 0°–5° C. for 2 hr. Thereafter, a solution of H-His-OMe.2HCl (14.56 g, 60 mmol) and N-ethylmorpholine (15.2 g, 16.89 ml, 132 mmol) in distilled DMF is added to the cold reaction mixture. The pH of the reaction mixture is adjusted to 8 and the reaction mixture stirred for 18 hr at 20°–22° C. The solid (N,N¹-dicyclohexylurea) is removed from the mixture by filtration. The filtrate is concentrated to dryness under reduced pressure. The residue is subjected to chromatography on silica gel (2400 g) using chloroform-methanolpyridine (89:10:1) as the eluant. The pure fractions are pooled and evaporated under reduced pressure to give 16.2 g of the title compound; NMR (CDCl$_3$) δ 3.70 (s, 3H), 5.12 (s, 2H), 7.25 (s, 5H); amino acid analysis: His (1.00), Pro (0.97).

EXAMPLE 2

Benzyloxycarbonyl-prolyl-histidyl-leucine, tert-Butyl Ester (Z-Pro-His-Leu-OBu$^t$)

Hydrazine hydrate (12.36 g, 12 ml, 0.25 mmol) is added to a solution of Z-Pro-His-OMe (10.0 g, 25 mmol, described in Example 1) at 0°–5° C. The solution is stirred at 20°–24° C. for 18 hr and then evaporated to dryness under reduced pressure. The residue is dissolved in methanol. Addition of diethyl ether to the solution precipitates Z-Pro-His-N$_2$H$_3$. A portion of the dipeptide hydrazide is crystallized from methanol-diisopropyl ether to give colourless crystals, mp 150°–160° C.; NMR(CDCl$_3$) δ 5.1 (s, 2H); amino acid analysis: His (1.0), Pro (0.95).

The dipeptide hydrazide (6.02 g, 15 mmol) is dissolved in distilled DMF (80 ml) and cooled to −15° C. Anhydrous hydrogen chloride in ethyl acetate (1.6 N, 46.87 ml, 5 eq) is added to the solution followed by the addition of t-butyl nitrite (3.12 g, 3.5 ml, 30 mmol). After stirring at −15° C. for 15 min, the reaction mixture is cooled to −30° C. and neutralized with N-ethyldiisopropyl amine (10.66 g, 14.1 ml, 82 mmol). Thereafter, a solution of H-Leu-OBu$^t$ (2.8 g, 15 mmol) in distilled DMF (10 ml) is added. The reaction mixture is stirred at −15° C. for 60 min, at ice-bath temperature for 60 min and at 20°–22° C. for 18 hr. The reaction mixture is concentrated under reduced pressure. The residue is triturated with diethyl ether and then subjected to chromatography on a silica gel (1000 g) using chloroform-methanol-pyridine (89:10:1) as the eluant. The pure fractions are pooled and evaporated to give 7.2 g of the title compound as an amorphous off-white solid; NMR(CDCl$_3$) δ 1.45 (s, 9H), 7.2 (s, 5H); amino acid analysis: Leu (1.00), His (1.04), Pro (1.02).

EXAMPLE 3

Benzyloxycarbonyl-seryl-leucine, tert-Butyl Ester (Z-Ser-Leu-OBu$^t$)

A solution of benzyloxycarbonyl-serine pentachlorophenyl ester (Z-Ser-OPcp, 19.5 g, 40 mmol) in distilled DMF (100 ml) is added at 0°–5° C. to a stirred solution of H-Leu-OBu$^t$ (7.5 g, 40 mmol) and HOBt (100 mg) in distilled DMF. The solution is kept at 0° C. for two days and then evaporated to dryness under reduced pressure. The residue is subjected to chromatography on silica gel (1300 g) using hexane-ethyl acetate (1:3) as the eluant. The pure fractions are pooled and evaporated to dryness to yield 11.39 g of the title compound; NMR(CDCl$_3$) δ 0.85 (m, 6H), 1.45 (s, 9H), 7.3 (s, 5H); amino acid analysis: Leu (1.00), Ser (0.93).

EXAMPLE 4

Benzyloxycarbonyl-prolyl-seryl-leucine, tert-Butyl Ester (Z-Pro-Ser-Leu-OBu$^t$)

A mixture of Z-Ser-Leu-OBu$^t$ (11.36 g, 27.8 mmol, described in Example 3) and 5% palladium on carbon (1.1 g) in glacial acetic acid is subjected to hydrogenation. The mixture is filtered and the filtrate is evaporated under reduced pressure to give H-Ser-Leu-OBu$^t$ in the form of its acetate salt. This product is suspended in toluene and the toluene is removed by distillation so that excess acetic acid is removed azeotropically.

For the next step the required activated ester is prepared as follows: DCC (7.03 g, 34 mmol) in distilled DMF is added dropwise at 0°–5° C. to a stirred solution of Z-Pro-OH (7.75 g, 31 mmol) and HOBt (6.28 g, 46.5 mmol) in distilled DMF (50 ml). The mixture is stirred at 0°–5° C. for 90 min to give a solution of the activated ester.

A solution of H-Ser-Leu-OBu$^t$.CH$_3$COOH (6.6 g, 19.7 mmol), prepared as described above, and N-ethylmorpholine (2.7 g, 3 ml, 24 mmol) is added to the above preparation of the activated ester at 0° C. The pH of the mixture is adjusted to 8 with N-ethylmorpholine and the mixture is stirred at 20°–24° C. for 18 hr. The solid (N,N¹-dicyclohexylurea) is removed from the mixture by filtration and the filtrate is concentrated to dryness under reduced pressure. The residue is purified on silica gel (1500 g) using hexane-chloroform (1:3) as the eluant. The pure fractions are pooled to yield 6.5 g of the title compound as a foam; NMR (CDCl$_3$) δ 0.9 (m, 6H), 1.45 (s, 9H), 7.3 (s, 5H); amino acid analysis: Leu (1.00), Ser (0.95), Pro (1.09).

EXAMPLE 5

N-[N-[1-(3-Acetylthio-1-oxopropyl)prolyl]histidyl]leucine, tert-Butyl Ester [CH$_3$COSCH$_2$CH$_2$CO-Pro-His-Leu-OBu$^t$]

A mixture of the protected tripeptide of formula III, Z-Pro-His-Leu-OBu$^t$ (5.9 g, 10.6 mmol, described in Example 2), and 5% palladium on carbon (600 mg) in glacial acetic acid is subjected to hydrogenation. The mixture is filtered and the filtrate evaporated under reduced pressure to give 5.2 g of H-Pro-His-Leu-OBu$^t$ in the form of its acetate salt. This product is suspended in toluene and the toluene then is removed by distillation so the excess acetic acid is removed azeotropically.

For the next step, the required activated ester is prepared as follows:

DCC (1.9 g, 9 mmol) is added in one portion to a cold solution of the acid compound of formula II, 3-acetylthiopropionic acid (1.33 g, 9 mmol), and HOBt in distilled DMF (20 ml). Thereafter, the mixture was stirred at 0°–5° C. for 60 min, and then at 20°–24° C. for 60 min.

A solution of H-Pro-His-Leu-OBu$^t$.CH$_3$COOH (1.82 g, 3.78 mmol), prepared and described above, and N-ethylmorpholine (522 mg, 0.58 ml, 4.5 mmol) in distilled DMF (20 ml) is added to the above preparation of the activated ester at 0° C. The pH of the mixture is adjusted to 8 with N-ethylmorpholine and the mixture is stirred at 20°-24° C. for 18 hr. The solid (N,N¹-dicyclohexylurea) is removed from the mixture by filtration. The filtrate is concentrated to dryness under reduced pressure. The residue is subjected to chromatography on silica gel (500 g) using chloroform-methanol-pyridine (89:10:1) as the eluant. The pure fractions are pooled and evaporated under reduced pressure to give 1.34 g of the title compound; NMR(CDCl$_3$) δ 1.45 (s, 9H), 2.35 (s, 3H); amino acid analysis: Leu (1.00), His (0.98), Pro (1.01); M+551.

By following the procedure of Example 5, but replacing 3-acetylthiopropionic acid with an equivalent amount of D-(−)-3-benzoylthioisobutyric acid, available from Chemical Dynamics Corporation, South Plainfield, New Jersey, U.S.A., 07080, N-[N-[1-(3-benzoylthio-2-D-methyl-1-oxopropyl)prolyl]histidyl]leucine, tert-butyl ester is obtained in a 54% yield. The latter compound has NMR(CDCl$_3$) δ 0.55 (m, 6H), 1.45 (s, 9H); amino acid analysis: Leu (1.00), Pro (0.99, His (0.97); M+627.

By following the procedure of Example 5, but replacing the protected tripeptide with one equivalent amount of Z-Pro-Ser-Leu-OBu$^t$, described in Example 4, and replacing 3-acetylthiopropionic acid with an equivalent amount of D-(−)-3-benzoylthioisobutyric acid, noted above, N-[N-[1-(3-benzoylthio-2-D-methyl-1-oxopropyl)prolyl]seryl]leucine, tert-butyl ester; NMR(CDCl$_3$) δ 2.85 (s, 9H); amino acid analysis: Leu (1.00), Ser (0.90), Pro (1.16); is obtained in a 52% yield.

EXAMPLE 6

N-[N-[1-(3-Mercapto-1-oxopropyl)prolyl]histidyl]leucine (HSCH$_2$CH$_2$CO-Pro-His-Leu-OH)

The protected thiotripeptide, CH$_3$COSCH$_2$CH$_2$CO-Pro-His-Leu-OBu$^t$, (0.6 g, 1.1 mmol, described in Example 5) is added under nitrogen to a solution of anisole (2 ml) and trifluoroacetic acid (23 ml) at 0°-5° C. The solution is stirred at 20°-24° C. for 150 min, during which time complete hydrolysis of the t-butyl ester is noted by tlc (MeOH/CHCl$_3$, 1:9). The volatile ingredients of the reaction mixture are removed by distillation under reduced pressure. The residue is dissolved in methanol (10 ml). The solution is treated at 0° C. under nitrogen with aqueous 1 N NaOH (4.47 ml). The solution is stirred at 20°-24° C. for 60 min, diluted with water (20 ml), and extracted with ethyl acetate (2×50 ml). The aqueous solution is adjusted to pH 4 with aqueous 1 N HCl and evaporated to dryness under reduced pressure. The residue is subjected to chromatography on silica gel (300 g) using chloroform-methanol-32% aqueous acetic acid (15:4:1) as the eluant. The pure fractions are pooled and evaporated under reduced pressure. The residue is dissolved in chloroform. Addition of diethyl ether to the solution precipitates the title compound, which is collected and dried. The title compound has NMR(CDCl$_3$) δ 0.75 (m, 6H); amino acid analysis: Leu (1.00), His (1.01), Pro (0.96).

By following the procedure of Example 6, but using N-[N-[1-(3-benzoylthio-2-D-methyl-1-oxopropyl)prolyl]histidyl]leucine, tert-butyl ester, described in Example 5, as the protected thiotripeptide, N-[N-[1-(3-mercapto-2-D-methyl-1-oxopropyl)prolyl]histidyl]leucine is obtained in a 90% yield. The latter compound has NMR(CDCl$_3$) δ 0.75 (m, 6H); amino acid analysis: His (1.00), Pro (0.93), Leu (1.05).

By following the procedure of Example 6, but using N-[N-[1-(3-benzoylthio-2-D-methyl-1-oxopropyl)prolyl]seryl]leucine, tert-butyl ester, described in Example 5, as the protected thiotripeptide, N-[N-[1-(3-mercapto-2-D-methyl-1-oxopropyl)prolyl]seryl]leucine is obtained in a 85% yield. The latter compound has mp 73°-78° C.; NMR(CDCl$_3$) δ 0.9 (m, 6H), 1.2 (d, 3H); amino acid analysis: Leu (1.00), Pro (1.06), Ser (0.89).

By following serially the procedures of Examples 5 and 6 and using the appropriate protected tripeptide of formula III and the appropriate acid compound of formula II, other compounds of formula I are obtained. For example, by employing Z-Pro-Phe-Arg(NO$_2$)-OMe as the protected tripeptide of formula III and D-(−)-3-benzoylthioisobutyric acid as the acid compound of formula II, N-[N-[1-(3-mercapto-2-D-methyl-1-oxopropyl)prolyl]phenylalanyl] arginine is obtained.

Likewise, by using Z-Pro-Arg-Ileu-OMe as the protected tripeptide of formula III and D-(−)-3-benzoylthioisobutyric acid as the acid compound of formula II, N-[N-[1-(3-mercapto-2-D-methyl-1-oxopropyl)prolyl]arginyl]isoleucine is obtained.

Likewise, by using Z-Pro-Tyr-Tyr-OMe as the protected tripeptide of formula III and D-(−)-3-benzoylthioisobutyric acid as the acid compound of formula II, N-[N-[1-(3-mercapto-2-D-methyl-1-oxopropyl)prolyl]tyrosyl]tyrosine is obtained.

Likewise, by using Z-Pro-Val-Pro-OMe as the protected tripeptide of formula III and D-(−)-3-benzoylthioisobutyric acid as the acid compound of formula II, N-[N-[1-(3-mercapto-2-D-methyl-1-oxopropyl)prolyl]valyl]proline is obtained.

We claim:

1. A compound of formula I

in which R$^1$ is hydrogen or lower alkyl; R$^2$ is an amino acid residue of alanine, arginine, cysteine, glycine, histidine, isoleucine, leucine, lysine, methionine, ornithine, phenylalanine, serine, threonine, tryptophan, tyrosine or valine; and R$^3$ is an amino acid residue of alanine, arginine, cysteine, glycine, histidine, isoleucine, leucine, lysine, methionine, ornithine, phenylalanine, proline, serine, threonine, tryptophan, tyrosine or valine; or a pharmaceutically acceptable salt thereof with an inorganic or organic base.

2. The compound of claim 1 in which R$^1$ is hydrogen or methyl.

3. The compound of claim 1 in which R$^1$ is hydrogen or methyl, and R$^2$ and R$^3$ are selected from the amino acid residues of arginine, histidine, leucine, phenylalanine and serine.

4. N-[N-[1-(3-Mercapto-1-oxopropyl)prolyl]histidyl]leucine, as claimed in claim 1.

5. N-[N-[1-(3-Mercapto-2-D-methyl-1-oxopropyl)prolyl]histidyl]leucine, as claimed in claim 1.

6. N-[N-[1-(3-Mercapto-2-D-methyl-1-oxopropyl)prolyl]seryl]leucine, as claimed in claim 1.

7. A pharmaceutical composition comprising a compound of claim 1 and a pharmaceutically acceptable carrier.

8. A method for alleviating angiotensin related hypertension in a hypertensive mammal which comprises administering to said mammal an effective dose of the compound of claim 1.

* * * * *